United States Patent [19]

Stapp

[11] 4,456,564
[45] Jun. 26, 1984

[54] RECOVERY OF PETROLEUM SULFONATE SALT

[75] Inventor: Paul R. Stapp, Bartlesville, Okla.

[73] Assignee: Phillips Petroleum Company, Bartlesville, Okla.

[21] Appl. No.: 78,528

[22] Filed: Sep. 24, 1979

[51] Int. Cl.³ ............................................. C07B 13/00
[52] U.S. Cl. ............................................. 260/504 S
[58] Field of Search ......................... 260/504 S, 504 R

[56] References Cited

U.S. PATENT DOCUMENTS 2,263,041 11/1941 Lazar et al. ................... 260/504 S
2,479,202 8/1949 Bransky et al. ................ 260/504 S Primary Examiner—Alan Siegel

[57] ABSTRACT

Deoiled monosulfonated oil salt is recovered from mass containing it together with unsulfonated oil, polysulfonated oil salt, and some mineral matter by diluting the mass with an aqueous-alcoholic solution, removing with a suitable solvent, an extract containing unsulfonated oil, then removing the alcohol and water from a thus-contained raffinate phase, diluting or dissolving thus-concentrated sulfonate salts with or in water and extracting with a suitable extraction solvent the mass thus obtained to remove therefrom an extract containing a concentration of monosulfonate salts.

10 Claims, No Drawings

RECOVERY OF PETROLEUM SULFONATE SALT

BRIEF SUMMARY OF THE INVENTION

A petroleum sulfonate salt is recovered in deoiled state from a mixture of it, unsulfonated oil and polysulfonate salts by steps including dilution of the crude sulfonation mass with an aqueous-alcoholic solution, extracting the diluted mass with an extractant suitable to remove unsulfonated oil, evaporating an extract obtained to remove water and alcohol therefrom, diluting with or dissolving in, water the salts thus recovered and extracting the solution thus obtained with another extractant suitable to produce an extract containing monosulfonate salt from which said salt can be recovered. The polysulfonate salts are concentrated in a raffinate phase thus obtained and can be recovered therefrom. Additional extractions on the recovered monosulfonate salts can be practiced for further purification. In one embodiment of the invention a mixture of mono- and polysulfonate salts dissolved in a mixture of methanol and water is extracted with pentane to remove into the pentane unsulfonated oil. The raffinate is evaporated to yield a residue containing mono- and polysulfonate salts and some mineral matter. The residue is extended with water and the solution thus obtained is extracted with n-butanol to obtain an extract which on evaporation yields a deoiled, monosulfonate-enriched product.

DETAILED DESCRIPTION

This invention relates to the production of a water soluble petroleum sulfonate. In one of its aspects it relates to a process for deoiling and recovering a water soluble monosulfonate salt of a petroleum oil. In a further aspect of the invention it relates to the recovery from a reaction mass containing the same of mono- and polysulfonate salts of petroleum substantially free from unsulfonated oil.

In one of its concepts, the invention provides a series of steps in combination including dilution of a crude sulfonation mass with an aqueous-alcoholic solution, extracting the diluted mass with an extractant suitable to remove unsulfonated oil, evaporating an extract thus obtained to remove water and alcohol therefrom, diluting with, or dissolving in, water the salts thus recovered and extracting the solution thus obtained with another extractant suitable to produce an extract containing monosulfonate salt. In another of its concepts, the invention provides a process wherein the monosulfonated salt can be further treated by one or more of the process steps described herein.

I have found that alkali metal or ammonium petroleum sulfonate salts can be isolated and recovered in a deoiled state from mixtures comprising unsulfonated oil and said petroleum sulfonates by a process comprising the dilution of the mixture with an aqueous solution of a lower alcohol such as methanol followed sequentially by extraction of the diluted mixture with a first hydrocarbon extractant such as pentane to remove unsulfonated oil, and evaporation of the extracted aqueous alcohol phase to recover a deoiled residue of said alkali metal or ammonium petroleum sulfonate salts. Further, these sulfonate salts can be refined by dissolving them in water and extracting the petroleum sulfonates therefrom with a second extractant such as n-butanol, and finally by evaporating the alcohol extract to recover deoiled, alkali metal or ammonium petroleum monosulfonate salts. The sulfonate salts recovered from this second extraction step are enriched in their monosulfonate content, the polysulfonate salts being largely retained in the raffinate.

The recovery of a product as herein described is important. For example, in post-primary oil recovery by surfactant flooding, a product as herein recovered is useful. Considering the energy shortfall now being experienced, it is important to make available all those processes or operations which most economically and effectively lead to the production of increased amounts of energy. Presently, and for a very long time into the foreseeable future, there is great dependency upon energy derived from oil. The post-primary oil recovery is now of great importance.

It is an object of this invention to provide a process for the recovery from an oil sulfonation reaction mass or equivalent mass, a deoiled, monosulfonated salt. It is another object of the invention to provide a combination of steps permitting the economic recovery of a sulfonated petroleum salt.

Other aspects, concepts, objects, and the several advantages of the invention are apparent from a study of this disclosure and the appended claims.

According to the present invention, a petroleum sulfonate salt is recovered in the deoiled state from a mixture of it, unsulfonated oil and polysulfonate salt by steps including dilution of the sulfonation mass with an aqueous-alcoholic solution, prepared employing a water soluble alcohol, extracting the diluted mass with an extractant suitable to remove unsulfonated oil, evaporating or stripping an extract thus obtained to remove water and alcohol therefrom, diluting with, or dissolving in, water the salts thus recovered and extracting the solution thus obtained with another extractant suitable to produce an extract containing monosulfonate salt.

The invention provides a process for deoiling concentrates of water soluble alkali metal and ammonium petroleum sulfonates from oil solution which may, e.g., be commercially available oil-containing concentrates of petroleum sulfonates suitable for use as surfactants in tertiary oil recovery processes. In addition, the invention procedure can be used in resolving unsulfonated oil and petroleum sulfonate mixtures arising, e.g., from the $SO_3$ sulfonation of sulfonatable hydrocarbon feedstocks wherein the reaction is carried out under anhydrous conditions in a diluent such as methylene chloride. Neutralization of the sulfonation reaction mass with an alkali metal hydroxide such as aqueous NaOH or ammonia either before or after stripping of the methylene chloride diluent provides a mixture of unsulfonated oil and petroleum sulfonates which can be resolved into unsulfonated oil and deoiled petroleum sulfonate components by application of the inventive procedure.

Alcohols suitable for dilution of the oil-sulfonate mixture prior to extraction of unsulfonated oil with saturated hydrocarbons include water soluble alcohols having up to about four carbon atoms such as methanol, ethanol, isopropanol, tert-butyl alcohol and diols and triols such as, respectively ethylene glycol and glycerol. Water-alcohol blends varying from 30:70 to 75:25 (v/v) are suitable for use in the present invention.

Saturated hydrocarbon first extractants suitable for the extraction of the alcohol-diluted unsulfonated oil/sulfonate mixture include alkanes containing 3 to 12 carbon atoms such as propane, butane, pentane, hexane, octane, decane, dodecane and the like as well as cycloalkanes such as cyclopentane and cyclohexane.

Second extractants suitable for the final refining of the mixed sulfonate residue involving the alcohol extraction of an aqueous sulfonate mixture include slightly water soluble alcohols such as n-butanol, 2-butanol, pentanols, hexanols, heptanols, octanols and the like as well as cycloalkanols such as cyclopentanol and cyclohexanol. In addition, selected aromatic solvents such as toluene, xylenes, chlorobenzene, nitrobenzene, benzonitrile and the like can also be used.

In the first step of the inventive process, the sulfonate/oil mixture is diluted with the above-described aqueous alcohols in proportions of from about 3 to 20 volumes per volume of sulfonate/oil mixture. The optimum proportions can vary depending upon the amount of sulfonate present and the nature of the oils but these can be determined by routine tests. This diluted mixture is then extracted with the hydrocarbon extractant described earlier using conventional liquid-liquid extraction procedures and apparatus in either the continuous or batch mode. The amount of hydrocarbon extractant will of course depend upon the mode of extraction and is largely a matter of convenience.

Stripping of the resultant hydrocarbon extract produces a largely unsulfonated oil product and a hydrocarbon solvent that can be recycled. Stripping of the raffinate produces a deoiled sulfonate product and water and alcohol that can be recycled. The sulfonate product is predominantly a mixture of monosulfonate salts and polysulfonate salts.

The deoiled monosulfonate/polysulfonate material obtained from the above can be subjected to the second step of the inventive process. It is first diluted with water in proportions of from about 3 to about 20 volumes per volume of sulfonate mixture. The optimum proportions can vary depending upon the nature of the sulfonate mixture but these can be determined easily by routine tests. This aqueous mixture is then extracted with a suitable extractant as described earlier using any convenient extraction procedure, apparatus, or mode.

Stripping the resultant extract solution produces deoiled sulfonate which has been enriched in its monosulfonate salt content. Stripping of the aqueous raffinate produces a predominantly polysulfonated product.

The composition of the commercially available petroleum sulfonates used in the Examples are as follows:

| (a) Witco Chemical Co. TRS 10-410 (Examples I, III, IV, V) | |
|---|---|
| Unsulfonated Oil | 34.0% |
| Active Sulfonate | 61.5% |
| Water | 4.4% |
| Inorganic Salts | 1.0% |
| (b) Stepan Chemical Co. Petrostep 465 (Example II) | |
| Unsulfonated Oil | 14.7% |
| Active Sulfonate | 59.4% |
| Water | 22.7% |
| Inorganic Salts | 3.2% |

Generally, according to the present invention, a sulfonated petroleum mass can be treated which may contain from about 10 to about 40% unsulfonated oil, from about 50 to about 65% active sulfonate, from about 1 to about 30% of water, and a small percentage of inorganic salt, e.g., from about 1 to about 4%. One skilled in the art in possession of this disclosure having studied the same can determine by mere routine tests the masses or sulfonates which can be treated to good advantage with the process of the invention. Similarly, such person can determine by mere routine test, diluents, solvents, and steps which can be substituted for those described herein.

The following inventive Example I demonstrates that the continuous pentane extraction of TRS 10-410 sample diluted with 250 ml of a 40:60 v/v water:methanol solution gave efficient recovery of unsulfonated oil. Evaporation of the extracted aqueous methanol mixture gave deoiled mono- and polysulfonates. Enrichment of monosulfonates into an alcohol phase, was effected by continuous n-butanol extraction of the mixed sulfonates in water. Evaporation of the alcohol extract provided a deoiled solid sample enriched in monosulfonates.

EXAMPLE I

A 17.7 g sample of Witco Chemical Co. TRS 10-410 petroleum sulfonates were dissolved in 150 ml of methanol and 100 ml of water and charged to a conventional glassware liquid-liquid extraction apparatus. This mixture was continuously extracted with n-pentane for a period of 24 hours. The pentane extract was stripped on a rotary evaporator to give 5.6 g of a liquid residue comprising pale yellow unsulfonated oil.

Evaporation of the aqueous methanol solution on a rotary evaporator yielded 11.9 g of a light tan solid. This solid comprising mono- and polysulfonates was dissolved in water and the aqueous mixture was charged to a continuous liquid-liquid extraction apparatus. This mixture was continuously extracted with n-butanol for a period of 24 hours. Evaporation of the separated n-butanol phase gave 11.3 g of a tan solid enriched in deoiled monosulfonates. An additional 0.5 g of tan solid enriched in polysulfonates and inorganic salts was recovered on evaporation of the water phase.

The following Example demonstrates that the continuous pentane extraction of a Stepan Petrostep 465 sample diluted with 250 ml of a 40:60 v/v water:methanol solution gave efficient removal of unsulfonated oil. Evaporation of the extracted aqueous methanol mixture gave deoiled mono- and polysulfonates.

EXAMPLE II

A 19.1 g sample of Stepan Petrostep 465 petroleum sulfonates was dissolved in a mixture of 150 ml of methanol and 100 ml of water and charged to a conventional glassware liquid-liquid extraction apparatus. This mixture was continuously extracted with pentane for a period of 24 hours. The pentane extract was stripped on a rotary evaporator to give 5.7 g of liquid residue comprising unsulfonated oil. An additional pentane extraction for 24 hours gave rise to 0.3 g of additional liquid residue comprising unsulfonated oil for a total recovery of 6 g.

Evaporation of the twice-extracted aqueous methanol solution of the rotary evaporator gave 12 g of a solid residue. This residue comprising mono- and poly-sulfonates and inorganic salts was dissolved in 200 ml of water and the aqueous mixture was charged to a continuous liquid-liquid extraction apparatus. This mixture was continuously extracted with n-butanol for a period of 24 hours. Evaporation of the separated n-butanol phase gave 8.6 g of a crystalline golden solid. On repeating the n-butanol procedure an additional 0.7 g of yellow solid was obtained giving a total yield of 9.3 g of deoiled sulfonate product. Evaporation of the aqueous phase gave 0.8 g of brown solid.

The following Example demonstrates that continuous pentane extraction of an aqueous mixture of TRS 10-410 containing no alcohol failed to recover unsulfonated oil.

EXAMPLE III

A 21.7 g sample of Witco Chemical Co. TRS 10-410 petroleum sulfonates was dissolved in 200 ml of water and charged to a conventional glassware liquid-liquid extraction apparatus. This mixture was continuously extracted with n-pentane for a period of 24 hours. The pentane extract was stripped on a rotary evaporator to give 0.04 g of residue. An additional 24 hour extraction of the aqueous mixture with pentane gave no unsulfonated oil.

The following Example illustrates that dilution of TRS 10-410 with 80:20 v/v water:methanol does not give a mixture from which unsulfonated oil can be extracted with pentane.

EXAMPLE IV

A 20.1 g sample of Witco Chemical Co. TRS 10-410 petroleum sulfonates was dissolved in a mixture of 50 ml of methanol and 200 ml of water and charged to a conventional glassware liquid-liquid extraction apparatus. This mixture was continuously extracted with n-pentane for a period of 24 hours. The pentane extract was stripped on a rotary evaporator to give 0.3 g residue.

The following Example illustrates that dilution of TRS 10-410 with 40:60 v/v water:methanol gives a mixture from which unsulfonated oil can be extracted with pentane. However, subsequent toluene extraction of the aqueous methanol mixture yielded essentially no deoiled petroleum sulfonates.

EXAMPLE V

A 19.1 g sample of Witco Chemical Co. TRS 10-410 petroleum sulfonates was dissolved in a mixture of 150 ml of methanol and 100 ml of water and charged to a conventional glassware liquid-liquid extraction apparatus. This mixture was continuously extracted with pentane for a period of 24 hours. The pentane extract was stripped on a rotary evaporator to give 7.1 g of liquid residue comprising unsulfonated oil.

The aqueous methanol solution was then continuously extracted with toluene for a period of 24 hours. Separation and evaporation of the toluene phase gave only 1.8 g of deoiled petroleum sulfonate residue. An additional toluene extraction of the remaining aqueous methanol mixture for 24 hours gave a toluene extract which on evaporation yielded 0.4 g of deoiled petroleum sulfonate residue.

Demonstrating the efficiency of the inventive deoiling process, the results of the inventive runs of Examples I and II, are summarized in Table I.

With regard to the results with Petrostep 465 in Example II the experimentally recovered weight of 5.7 g for the pentane-extracted material indicates that the pentane extraction was continued perhaps too long and some petroleum sulfonates were taken into the pentane extract. Perhaps a 12 hour rather than 24 hour pentane extraction would have been sufficient. In view of this rationale, it is not surprising that the observed amount of deoiled sulfonate (9.3 g) is less than the theory value of 11.3 g.

Reasonable variation and modification are possible within the scope of the foregoing disclosure and the appended claims to the invention the essence of which is that a mixture of monosulfonates, polysulfonates, and unsulfonated oil are treated in a series of steps to recover a monosulfonated oil salt by diluting such a mixture with an aqueous-alcoholic solution extracting with a suitable extractant unsulfonated oil, removing substantially water and alcohol from a remaining raffinate phase, diluting or dissolving salts thus concentrated with or in water and extracting the mass thus obtained with an extractant suitable to yield an extract containing a concentration of monosulfonate salt.

I claim:

1. A process for the recovery of deoiled monosulfonated oil salt from a mass containing it together with unsulfonated oil, polysulfonated oil salt and some mineral matter which comprises diluting the mass with an aqueous-alcoholic solution, extracting the diluted mass with an extractant suitable to remove therefrom an extract containing unsulfonated oil, removing substantially the alcohol and water from a remaining raffinate phase, diluting or dissolving sulfonate salts, thus concentrated, with or in water, and extracting the mass thus obtained with another extractant suitable to remove therefrom an extract containing a concentration of monosulfonate salt.

2. A process according to claim 1 wherein the mass treated essentially comprises at least one of a water soluble alkali metal and a water soluble ammonium petroleum sulfonate in unsulfonated oil.

3. A process according to claim 1 wherein the mass treated has been obtained from the SO3 sulfonation of sulfonatable hydrocarbon feed stock and the sulfonation reaction mass has been neutralized with at least one of an alkali metal hydroxide and ammonia.

4. A process according to claim 1 wherein the mass is diluted with at least one of a water soluble alcohol having up to about 4 carbon atoms, a diol and a triol.

5. A process according to claim 1 wherein the raffinate salts which have been concentrated and diluted in water are now extracted with at least one of a slightly water soluble alcohol and an aromatic solvent.

TABLE I

| | | Deoiling Petroleum Sulfonates | | | | | | | |
|---|---|---|---|---|---|---|---|---|---|
| | | TRS 10-410[a] | | | | Petrostep 465[b] | | | |
| | | Wt. Unsulfonated Oil | | Wt. Active Sulfonate | | Wt. Unsulfonated Oil | | Wt. Active Sulfonate | |
| Run No. | Example | Theory | Recovered | Theory | Recovered | Theory | Recovered | Theory | Recovered |
| 1 | I | 6.0 | 5.6 | 10.9 | 11.3 | | | | |
| 2 | II | — | — | — | — | 2.8 | 5.7 | 11.3 | 9.3 |

[a]The theory values for TRS 10-410 were calculated as follows:
(1) unsulfonated oil: sample weight of 17.7 g × 34% = 6.0 g and
(2) active sulfonate: sample weight of 17.7 g × 61.5% = 10.9 g.
[b]The theory values for Petrostep 465 were calculated as follows:
(1) unsulfonated oil: sample weight of 19.1 g × 14.7% = 2.8 g and
(2) active sulfonate: sample weight of 19.1 g × 59.4% = 11.3 g.

6. A process according to claim 4 wherein the water soluble alcohol is at least one selected from the following:
- methanol
- ethanol
- isopropanol
- tertiary-butyl alcohol
- ethylene glycol and
- glycerol.

7. A process according to claim 5 wherein the extractant is at least one selected from the following:
- n-butanol
- 2-butanol
- pentanol
- hexanol
- heptanol
- octanol
- cycloalkanol
- toluene
- xylene
- chlorobenzene
- nitrobenzene and
- benzonitrile.

8. A process according to claim 1 wherein the aqueous-alcoholic solution contains water and alcohol in proportions varying from about 30:70 to about 75:25, on a volume basis.

9. A process according to claim 1 wherein the mass treated is diluted with the aqueous-alcoholic solution in proportions of from about 3 to about 20 volumes per volume of said mass.

10. A process according to claim 1 wherein the aqueous alcohol solution is prepared employing methanol, the extractant contacted with the solution obtained is normal pentane and wherein the extractant contacted with the water diluted or dissolved sulfonate salts is n-butanol.

* * * * *